United States Patent [19]

Boocock et al.

[11] 4,400,298

[45] Aug. 23, 1983

[54] WOOD PRESERVATIVE COMPOSITIONS

[75] Inventors: Denis Boocock, Middlesex; Barbara M. Kimber, London, both of England

[73] Assignee: Borax Holdings Limited, London, England

[21] Appl. No.: 293,072

[22] Filed: Aug. 17, 1981

Related U.S. Application Data

[63] Continuation-in-part of Ser. No. 158,970, Jun. 12, 1980, abandoned, which is a continuation-in-part of Ser. No. 968,834, Dec. 12, 1978, abandoned.

[30] Foreign Application Priority Data

Dec. 16, 1977 [GB] United Kingdom ............... 52415/77

[51] Int. Cl.³ ..................... A01N 59/14; A01N 59/02; A01N 37/44; A01N 37/02; A01N 33/08
[52] U.S. Cl. ............................... 252/400 R; 424/148; 424/175; 424/185; 424/286; 424/300; 106/18.3; 106/18.33
[58] Field of Search ............... 252/380, 383, 384, 385, 252/400 R, 402, 400.4, 400.62; 106/15 R, 18.3, 18.33; 424/148, 175, 185, 286, 300

[56] References Cited

U.S. PATENT DOCUMENTS

| | | | |
|---|---|---|---|
| 1,972,961 | 9/1934 | Tisdale et al. | 424/286 |
| 2,186,134 | 1/1940 | Chapman | 424/148 |
| 2,392,987 | 1/1946 | Hill | 424/148 |
| 2,791,605 | 5/1957 | Dorman et al. | 424/286 |
| 2,792,327 | 5/1957 | Hunt | 424/286 |
| 2,929,758 | 5/1960 | Buckman et al. | 424/286 |
| 2,945,781 | 7/1960 | Santmyer | 424/286 |
| 3,007,844 | 11/1961 | Schulz et al. | 424/148 |
| 3,167,471 | 1/1965 | Kovacs et al. | 424/286 |
| 3,312,725 | 4/1967 | Weissenberger | 424/185 |
| 3,973,034 | 8/1976 | Buckman et al. | 424/256 |
| 4,038,288 | 7/1977 | Lies et al. | 424/300 |

FOREIGN PATENT DOCUMENTS

| | | | |
|---|---|---|---|
| 2853557 | 6/1979 | Fed. Rep. of Germany | 424/286 |
| 861043 | 2/1961 | United Kingdom | 424/286 |
| 1486174 | 9/1977 | United Kingdom | 424/300 |
| 2013498 | 8/1979 | United Kingdom | 424/286 |

OTHER PUBLICATIONS

The Merck Index, 8th Ed., p, 965, (1965).

*Primary Examiner*—Teddy S. Gron
*Attorney, Agent, or Firm*—James R. Thornton

[57] ABSTRACT

Compositions for preventing or inhibiting the infection of wood raw materials by fungi causing sapstain, superficial mold and decay comprising a mixture of a dithiocarbamate, an alkali metal borate, and a selected antioxidant stabilizing agent. The mixtures exhibit a synergistic fungicidal activity and have the advantage over known anti-stain wood-preservative compounds that they are stable, relatively non-toxic and water-soluble. The compositions may be formulated as a dry formulation, as a solution or as a gel and may also include an alkaline salt or a gelling agent.

21 Claims, No Drawings

WOOD PRESERVATIVE COMPOSITIONS

This is a continuation-in-part of our copending application Ser. No. 158,970 filed June 12, 1980, now abandoned, which in turn is a C-I-P of our application Ser. No. 968,834 filed Dec. 12, 1978, now abandoned.

This invention relates to wood preservative compositions and their use to prevent the infection of freshly felled or sawn timber by the fungi which cause sapstain, superficial mold and decay.

In recent years, much attention has been centered on finding new compounds for the protection of wood raw material. Previously, the wood products industry was largely dependent on chlorinated phenols for control of sapstain. However, chlorinated phenols, such as pentachlorophenol, are now considered to pose a threat to manufacturers, users and to the environment. Antistain wood preservatives containing sodium pentachlorophenate have already been withdrawn from the market in some countries such as Sweden.

There is, therefore, a need for a composition for the protection of freshly felled or sawn timber which avoids the serious problem of toxicity posed by the use of chlorinated phenols. Other classes of compounds have been proposed, but many have the disadvantage that they are practically insoluble in water. This means that for their practical application provision must be made to keep them in suspension.

An object of the present invention is, therefore, to provide a stable composition which is not only relatively non-toxic but which is also water-soluble.

A further object is to provide a composition which is effective not only against sapstain but also against mold, fungi and decay.

To this end, we have found a composition which prevents or inhibits the infection of wood raw material such as freshly felled or sawn timber by the organisms which cause sapstain, superficial mold and decay during storage or seasoning of green timber, the composition comprising as one active ingredient a substituted dithiocarbamate.

Many dithiocarbamic acid salts have been described in the chemical literature as commercial industrial and agricultural microbiocides and nematocides. For example, United Kingdom Pat. No. 1,420,028 and U.S. Pat. Nos. 3,973,034, 3,167,471 and 1,972,961 describe pesticidal compositions containing dithiocarbamates. According to U.S. Pat. No. 3,973,034, the pesticidal composition comprises an active material which is the reaction product of a dithiocarbamate with formaldehyde. Example III shows that the compositions are less effective when the dithiocarbamate has not been reacted with formaldehyde. The compositions according to U.S. Pat. No. 3,973,034 are stated to have very wide application. In general, the compositions may be used for inhibiting the growth or proliferation of bacteria or fungi in organic substances susceptible to microbiological deterioration in the presence of moisture but there is not reference to their use on wood raw material.

We have now, surprisingly, found a composition which is effective in preventing or inhibiting the infection of wood raw material by the fungi which cause sapstain, superficial mold and decay. The composition comprises as active ingredients an optionally substituted dithiocarbamate and an alkaline borate stabilized with a specific antioxidant. We have found that this mixture exhibits a synergistic fungicidal action.

Accordingly, the invention provides a composition which comprises as active ingredients, an alkali metal borate and a dithiocarbamate of the general formula:

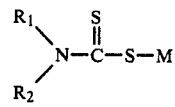

wherein $R_1$ and $R_2$ are the same or different and represent hydrogen or an alkyl group containing 1-5 carbon atoms and M represents an alkali metal, ammonium or substituted ammonium group. The ammonium group substituents are the lower alkyl groups such as $C_{1-3}$ alkyl.

The compositions according to the present invention are less hazardous to the environment and more easily and safely handled by the operator than previously used compositions containing chlorinated phenols. The compositions according to the invention are water soluble and have been found to be effective in preventing the growth of the fungi which cause discoloration found on unseasoned timber known as sapstain or blue-stain, superficial mold and wood-rotting basidiomycetes.

In particular, as exemplified herein, we have found that the compositions according to the present invention are effective in preventing or inhibiting sapstain and decay caused by *Cladosporium herbaru*, *Ceratocystis pilifera*, *Ceratocystic picea*, *Aureobasidium pullulans*, *Scopularia phycomyces*, Sclerophoma pithyophila and the white rot fungus *Phlebia gigantea*; mold growth caused by *Trichoderma lignorum*, Penicillium spp. (2 species), Alternaria sp., Cladosporium sp., *Cladosporium sphae sporium*; Aspergillus sp. and the thermo-tolerant mold Rhizopus sp. which occurs in kilns. The compositions have also been shown to be effective in practical situations where untreated timber in the same tests was heavily colonized by a wide range of stain, decay and mold fungi.

Typical examples of suitable substituted dithiocarbamates are sodium dimethyldithiocarbamate, dimethyl ammonium dimethldithiocarbamate and sodium N-ethyldithiocarbamate. The preferred dithiocarbamate is sodium dimethyldithiocarbamate.

Typical examples of alkali metal borates for use in the composition according to this invention are anhydrous borax, borax (sodium tetraborate decahydrate), borax pentahydrate (sodium tetraborate pentahydrate), sodium metaborate, potassium metaborate, sodium pentaborate, POLYBOR ® ($Na_2B_8O_{13}.4H_2O$) and potassium pentaborate.

The compositions of the invention preferably comprise the mixture of the active ingredients, alkali metal borate and dithiocarbamate, in a parts by weight ratio of about 3:1 to 1:3; the alkali metal borate being expressed as anhydrous borax. A particularly preferred ratio is in the range of 0.5 to 2.5 parts by weight of dithiocarbamate to 1 part by weight of anhydrous borax equivalent.

A stabilizer is also present to prevent the formation of a precipitate in solutions of the present compositions. The stabilizer is an antioxidant selected from the alkali metal sulfites, such as sodium sulfite and potassium metabisulfite, and sodium lower alkyl xanthates, such as sodium isopropyl xanthate, and is present at a level corresponding to about 1 to 5 percent of the dithiocarbamate. Potassium metabisulfite is the presently preferred stabilizer.

The compositions of the invention are contacted with timer in an amount sufficient to prevent the growth of sapstain, mold and wood decaying basidiomycetes. They preferably are applied dissolved in a liquid carrier such as water. The solutions for wood treatment contain from about 0.5 to 5.0% w/v substituted dithiocarbamate and from about 0.25-2.5% w/v alkali metal borate expressed as anhydrous borax. For most applications, the solutions contain 1.0-3.0% w/v dithiocarbamate and 0.5-2.0% w/v anhydrous borax equivalent. Larger quantities of borate can be used but no further advantage is gained in controlling fungal growth. The stabilizers are present at a level in the range of from about 0.2 to 2% w/w of the aqueous solutions, preferably in the range of about 0.3 to 0.6%.

The compositions of the invention can be prepared as dry formulations or they can be dissolved or dispersed in a liquid carrier for subsequent dissolution and/or dilution to the required working concentration for treating timber.

Dry formulations can be prepared, for example, by mixing together the dithiocarbamate with a water deficient alkali metal borate such as borax pentahydrate.

In another aspect of the invention, dry formulations may be prepared by mixing a concentrated aqueous solution of the dithiocarbamate (containing about 40% w/w dithiocarbamate) with a water deficient alkali metal borate, a water deficient alkaline salt and optionally a neutral water deficient salt; for example, anhydrous sodium or magnesium sulphate. Excess water can be evaporated by hot air drying.

According to another particular embodiment of the invention, the composition is formulated as a gel and comprises a gelling agent such as carboxymethyl cellulose or a derivative thereof, e.g., STAFLO. A preferred gel composition according to the invention comprises sodium dimethyldithiocarbamate, sodium metaborate ($Na_2B_2O_4.8H_2O$), STAFLO and anhydrous sodium sulphite.

The pH of the aqueous solutions according to this invention is above 10, preferably up to 13.2. At these pH ranges, greater stability is imparted to the solutions since we have found that at a lower pH precipitation of a crystalline material may occur in solutions which have been standing several days. The pH can be controlled by the amount of alkali metal borate present or by addition of other alkaline salts such as sodium carbonate, trisodium phosphate, the tetrasodium salt of ethylenediaminetetraacetic acid and sodium acetate.

Liquid formulations may be prepared by dissolving or dispersing the alkali metal borate, dithiocarbamate and stabilizer in a liquid carrier, such as water, to form either a concentrated solution, slurry or paste for subsequent dilution to the required working concentration. As in the dry formulations, alkaline salts and neutral salts may be employed as ingredients of the liquid compositions.

In a further aspect of the invention, a polyhydroxy compound may be included in the liquid formulations to complex the borate and thereby increase the concentration of borate stable in solution. Glycerol is a preferred polyhydroxy compound for this application.

The invention is further illustrated by the following examples:

EXAMPLE 1

Aqueous solutions were made up to the following formulations:

A 2% w/v dimethylammonium dimethyldithiocarbamate, 2% w/v borax.
B 1% w/v sodium dimethyldithiocarbamate, 2% w/v borax.
C 2% w/v sodium dimethyldithiocarbamate, 2% w/v borax.
D 2% w/v dimethylammonium dimethyldithiocarbamate.
E 2% w/v sodium dimethyldithiocarbamate.
F 2% w/v borax.
G water.

The following tests were carried out to determine the effect of compositions according to the present invention on the growth of fungi on samples of freshly sawn, unseasoned timber.

Twenty-five pieces of freshly sawn, stain-free, Scotch pine, approximately $12'' \times 4'' \times 1''$ in size, which consisted predominantly of sapwood, were individually immersed in each test solution for ten seconds and then allowed to drain. Each series of samples were close stacked, $5 \times 5$, and covered with polyethylene sheet. After two weeks, the polyethylene cover was removed. The stacks were broken after six weeks and assessed on the scale 0–5 where 0 = nil infection
1 = trace
2 = light
3 = moderate
4 = heavy
5 = very heavy The stacks were assessed for a second time after a further four weeks. The results of the assessments were recorded as in Table I. Note that the order of the pieces in the table is not significant since each piece within the test was not labeled.

These tests relied on the prevention of sapstain, surface mold and decay under severe natural conditions. The untreated control samples were infected by sapstain and surface molds from which Penicillium spp, Trichoderma sp. and *Aspergillus niger* were positively identified. A wood rotting basidiomycete, Peniophora sp., was also identified.

TABLE I

| Solution | Assessment | | | | | | | | | | | | | | | | | | | | | | | | Remarks | Total |
|---|---|---|---|---|---|---|---|---|---|---|---|---|---|---|---|---|---|---|---|---|---|---|---|---|---|---|
| A | St. | 1st | 0 | 0 | 0 | 0 | 0 | 0 | 1 | 1 | 0 | 0 | 0 | 0 | 0 | 0 | 0 | 0 | 0 | 0 | 3 | 0 | 0 | 0 | 1 | (a) | 13 |
| | | 2nd | 0 | 1 | 0 | 0 | 2 | 2 | 1 | 3 | 2 | 2 | 2 | 0 | 0 | 3 | 3 | 0 | 0 | 0 | 3 | 2 | 0 | 0 | 2 | | 21 |
| | Bas. | 1st | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| | | 2nd | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| B | St. | 1st | 2 | 2 | 0 | 0 | 0 | 0 | 0 | 0 | 0 | 0 | 0 | 0 | 0 | 0 | 0 | 0 | 0 | 0 | 0 | 1 | 0 | 0 | 0 | mostly mold | 5 |
| | | 2nd | 0 | 0 | 2 | 0 | 2 | 2 | 0 | 0 | 0 | 0 | 1 | 0 | 0 | 0 | 1 | 0 | 0 | 1 | 0 | 0 | 0 | 2 | 0 | little stain | 11 |
| | Bas. | 1st | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| | | 2nd | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| C | St. | 1st | 0 | 0 | 0 | 0 | 0 | 0 | 0 | 0 | 0 | 0 | 0 | 0 | 0 | 0 | 0 | 2* | 2* | 0 | 0 | 0 | 0 | 0 | 0 | mold | 4 |
| | | 2nd | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | *trichoderma | 6 |
| | Bas. | 1st | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| | | 2nd | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| D | St. | 1st | 2 | 2 | 0 | 1 | 0 | 4 | 4 | 3 | 0 | 1 | 0 | 1 | 0 | 0 | 1 | 0 | 0 | 2 | 0 | 1 | 4 | 0 | 0 | trichoderma | 27 |
| | | 2nd | 2 | 3 | 2 | 4 | 3 | 3 | 1 | 2 | 3 | 0 | 3 | 0 | 2 | 2 | 3 | 0 | 0 | 3 | 3 | 0 | 0 | 0 | 0 | | 39 |
| | Bas. | 1st | 2 | 2 | 0 | 0 | 0 | 0 | 0 | 0 | 2 | 0 | 2 | 0 | 2 | 0 | 2 | 2 | 2 | 2 | 0 | 0 | 0 | 0 | 0 | | 16 |
| | | 2nd | 3 | 3 | 4 | 4 | 3 | 0 | 0 | 0 | 3 | 0 | 3 | 0 | 3 | 0 | 3 | 0 | 0 | 3 | 0 | 2 | 4 | 2 | 0 | | 40 |
| E | St. | 1st | 0 | 0 | 0 | 0 | 0 | 0 | 0 | 0 | 0 | 0 | 0 | 0 | 0 | 0 | 2 | 2 | 2 | 0 | 2 | 0 | 0 | 0 | 0 | (b) | 25 |
| | | 2nd | 0 | 0 | 0 | 0 | 0 | 0 | 2 | 3 | 2 | 2 | 0 | 0 | 0 | 0 | 2 | 2 | 2 | 2 | 2 | 0 | 0 | 3 | 0 | | 21 |
| | Bas. | 1st | 2 | 2 | 1 | 2 | 2 | 1 | 1 | 0 | 2 | 2 | 2 | 0 | 2 | 0 | 0 | 0 | 0 | 2 | 0 | 2 | 0 | 0 | 0 | | 17 |
| | | 2nd | 3 | 3 | 3 | 1 | 3 | 2 | 2 | 1 | 0 | 3 | 3 | 0 | 2 | 0 | 2 | 2 | 2 | 3 | 2 | 3 | 0 | 3 | 0 | | 21 |
| F | St. | 1st | 0 | 0 | 0 | 0 | 0 | 3 | 4 | 0 | 4 | 4 | 0 | 4 | 0 | 2 | 0 | 2 | 3 | 0 | 4 | 0 | 4 | 4 | 3 | *mostly | 46 |
| | | 2nd | 0* | 0* | 0* | 0* | 0* | 0* | 0 | 0 | 4 | 4 | 4 | 4 | 4 | 4 | 4 | 4 | 0 | 2 | 3 | 0 | 0 | 3 | 0 | heartwood | 47 |
| | Bas. | 1st | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| | | 2nd | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| G | St. | 1st | 4 | 5 | 5 | 5 | 5 | 5 | 5 | 5 | 4 | 5 | 5 | 5 | 5 | 5 | 5 | 5 | 5 | 5 | 5 | 5 | 5 | 5 | 5 | | 115 |
| | | 2nd | 5 | 4 | 5 | 5 | 5 | 5 | 5 | 5 | 5 | 5 | 5 | 5 | 5 | 5 | 5 | 5 | 5 | 5 | 5 | 5 | 5 | 5 | 5 | | 125 |
| | Bas. | 1st | 3 | 3 | 3 | 3 | 3 | 2 | 2 | 2 | 2 | 2 | 2 | 2 | 2 | 3 | 3 | 3 | 3 | 3 | 3 | 3 | 3 | 3 | 3 | | 59 |
| | | 2nd | 4 | 4 | 5 | 4 | 3 | 3 | 3 | 3 | 2 | 3 | 0 | 3 | 4 | 4 | 3 | 3 | 3 | 3 | 3 | 3 | 3 | 3 | 3 | | 66 |

Remarks:
(a) Mainly penicillium sp., no stain
(b) Basidiomycetes as mycelia and brown pockets
NOTES ON TABLE I:
Bas. = Basidiomycetes.
St. = Sapstain and mold.
1st = First assessment after 6 weeks.
2nd = Second assessment after 10 weeks.

The results tabulated in Table I show the synergistic action of the mixture of alkali metal borate and dithiocarbamate. Thus, where solutions of a dithiocarbamate alone were used (solutions D and E), the results showed many instances of infection varying from trace to heavy infection. However, where mixtures of the dithiocarbamate with an alkali metal borate were employed (solutions A, B and C) there were only a few instances of infection and, in the specific case of the assessment for basidiomycetes infection, the results showed nil infection in all samples even for the second assessment performed four weeks after the first.

The following are additional examples of suitable fungicidal compositions for preventing sapstain, mold and decay in unseasoned timber, in which all components are expressed as parts by weight.

EXAMPLE 2

| | |
|---|---|
| Sodium dimethyldithiocarbamate (40% w/w in water) | 61.8 |
| Sodium metaborate ($Na_2B_2O_4.8H_2O$) | 37.7 |
| STAFLO (carboxymethyl cellulose, gelling agent) | 1.25 |
| Sodium sulphite, anhydrous | 1.25 |

EXAMPLE 3

| | |
|---|---|
| Sodium metaborate octahydrate | 11.6 |
| Glycerol | 7.7 |
| 40% w/w sodium dimethyldithiocarbamate | 20.0 |

EXAMPLE 4

| | |
|---|---|
| Sodium metaborate octahydrate | 15.0 |
| 40% w/w sodium dimethyldithiocarbamate | 37.0 |
| Sodium isopropyl xanthate | 0.5 |
| Water | 50.0 |

EXAMPLE 5

| | |
|---|---|
| Borax pentahydrate | 50.0 |
| Sodium dimethyldithiocarbamate dihydrate | 50.0 |
| Sodium sulfite | 1.0 |

EXAMPLE 6

| | |
|---|---|
| Borax (fine powder) | 20.0 |
| Sodium dimethyldithiocarbamate dihydrate | 20.0 |
| Anhydrous sodium carbonate | 10.0 |
| Sodium sulfite | 0.5 |
| Water | 8.0 |

EXAMPLE 7

| | |
|---|---|
| Sodium dimethyldithiocarbamate | 20.0 |
| Potassium metaborate | 20.0 |
| Sodium sulphite | 0.5 |
| Water | 59.5 |

EXAMPLE 8

| | |
|---|---|
| Potassium metaborate | 15.5 |
| Sodium dimethyldithiocarbamate | 20.0 |
| Potassium metabisulfite | 0.9 |
| Water | 63.6 |

Example 8 represents a preferred composition of this invention. The potassium metaborate can be prepared in situ from a 50% solution of potassium hydroxide and boric acid according to the equation:

$$2KOH + 2H_3BO_3 \rightarrow K_2B_2O_4 + 4H_2O$$

After formation of the potassium metaborate, the solution is diluted with water and the other ingredients added. The pH of the resultant solution preferably is in the range of 12.5 to 13.1 (determined at 20°±2° C.). Care should be exercised to avoid the formation of seed crystals which will promote crystallization at low temperatures.

The compositions of Example 6-8 are concentrates which are preferably diluted with water prior to use so as to obtain solutions containing about 2 to 10% w/v of the borate-carbamate combination.

EXAMPLE 9

The following laboratory tests were performed with the composition of Example 2 against sapstain, decay and mold growth on green pine (*Pinus silvestris*, L.) wood.

The tests were carried out on freshly sawn discs of Scotch pine (*Pinus silvestris* L.). In principle, a method described in Report No. 75 from the Swedish Wood Preservation Committee was followed. The method involves treatment of the discs with a spore suspension of the test fungi and a dip treatment in water solutions or water mixtures of the compositions in various concentrations. Sodium pentachlorophenate was included in the test for comparison.

After inoculation and preservative treatment, the discs were placed in a moist chamber at the ambient room temperature (usually 20°-22° C.). The discs were examined once a week for a three-week period. The fungal growth was evaluated on each disc according to a scale from 0 to 2, where 2 means fungal growth or discoloration over the whole disc. For each series, an average index is then calculated. This index is reported in the attached tables.

The tests were carried out in three separate parts.

A. Sapstain and decay. The discs were inoculated with a mixture of four staining fungi (*Cladosporium herbarum, Ceratocystis pilifera, Aureobasidium pullulans, Scopularia phycomyces*) and the white rot fungus *Phlebia gigantea*.

B. Mold growth. The discs were inoculated with a mixture of six mold fungi—*Trichoderma lignorum*, Penicillium spp. (2 species), Alternaria sp., Cladosporium sp., *Cladosporium sphaerosporium*.

C. Thermotolerant mold. The discs were inoculated with the thermotolerant mold fungus Rhizopus sp. and incubated for 4 days at +40° C. The discs were examined daily.

The results obtained are tabulated in the following Tables II to IV, inclusive.

TABLE II

TESTING OF COMPOSITION
AGAINST SAPSTAIN AND DECAY
Development of Sapstain and Decay After the Incubation Period

| Treatment | Conc. (%) | 1 Week Stain | 1 Week Decay | 2 Weeks Stain | 2 Weeks Decay | 3 Weeks Stain | 3 Weeks Decay |
|---|---|---|---|---|---|---|---|
| Control | 0 | 2.0 | 0 | 2.0 | 1.2 | 2.0 | 1.7 |
| Na—PCP* | 1.0 | 0.3 | 0 | 0.8 | 0 | 0.8 | 0 |
| | 1.5 | 0.2 | 0 | 0.7 | 0 | 0.5 | 0 |
| | 2.0 | 0 | 0 | 0.2 | 0 | 0.3 | 0 |
| | 2.5 | 0 | 0 | 0 | 0 | 0.5 | 0 |
| Composition of Example 2 | 2.0 | 0 | 0 | [1]0.8 | 0 | [1]1.0 | 0 |
| | 4.0 | 0 | 0 | [1]0.3 | 0 | [1]0.2 | 0 |
| | 8.0 | 0 | 0 | [2]0.2 | 0 | [1]0.2 | 0 |
| | 12.0 | 0 | 0 | 0 | 0 | [1]0 | 0 |
| | 15.0 | 0 | 0 | 0 | 0 | [1]0 | 0 |
| | 20.0 | 0 | 0 | 0 | 0 | [1]0 | 0 |
| Control | 0 | 2 | 0 | 2 | 1.0 | 2 | 1.0 |

[1]Slight mold infection
[2]One of the discs infected by molds
*Sodium pentachlorophenate, for comparison

TABLE III

TESTING OF THE COMPOSITIONS
AGAINST MOLD FUNGI

| Treatment | Conc. (%) | 1 week | 2 weeks | 3 weeks |
|---|---|---|---|---|
| Control | 0 | 1.7 | 2.0 | 2.0 |
| Na—PCP* | 1.0 | 0.5 | [2]1.0 | 1.0 |
| | 1.5 | [1]0 | [2]0.7 | 1.0 |
| | 2.0 | [1]0 | [2]0.2 | 0.7 |
| | 2.5 | 0 | [1]2 0 | 0.8 |
| | 3.0 | [1]0 | [2]0.2 | 1.0 |
| Composition of Example 2 | 2.0 | 1.3 | 1.7 | 1.5 |
| | 4.0 | 0.7 | 1.2 | 1.2 |
| | 8.0 | [1]0 | [1]0.2 | 0.5 |
| | 12.0 | 0.2 | [1]0.2 | [3]0.7 |
| | 15.0 | [1]0 | [1]0.2 | [3]0.8 |
| | 20.0 | [1]0 | [1]0.2 | [3]0.8 |
| Control | 0 | 2.0 | 2.0 | 2.0 |

[1]Sparse growth on the cambial area
[2]Trichoderma
[3]Growth, mainly on the cambial area
*Sodium pentachlorophenate, for comparison

TABLE IV

TESTING OF THE COMPOSITION
AGAINST RHIZOPUS SP.

| Treatment | Conc. (%) | 1 day | 2 days | 3 days | 4 days |
|---|---|---|---|---|---|
| Control | 0 | 2.0 | 2.0 | 2.0 | 2.0 |
| Na—PCP* | 1.0 | 0.2 | 1.2 | 1.0 | 1.3 |
| | 1.5 | 0 | 0.8 | 1.0 | 1.2 |
| | 2.0 | 0 | 0.7 | 0.8 | 0.8 |
| | 2.5 | 0 | 0.5 | 0.7 | 0.8 |
| | 3.0 | 0 | 0 | 0 | 0 |
| Composition of Example 2 | 2.0 | 0 | [1]0.5 | 1.0 | 1.3 |
| | 4.0 | 0 | [2]0 | [1]0.3 | 0.8 |
| | 8.0 | 0 | 0 | 0 | 0 |
| | 12.0 | 0 | 0 | 0 | 0 |
| | 16.0 | [3]0 | [3]0 | [3]0 | [3]0 |
| | 20.0 | [3]0 | [3]0 | [3]0 | [3]0 |
| Control | 0.0 | 2.0 | 2.0 | 2.0 | 2.0 |

[1]Growth on the cambial area
[2]Sparse growth on the cambial area
[3]Brown discoloration of certain discs (non-microbial origin)
*Sodium pentachlorophenate, for comparison The results reported in Tables II to IV show that the effect of the composition according to the invention in the selected concentration range was very good against sapstain and the development of *Phlebia gigantea*. The latter fungus was totally inhibited in all the tested concentrations and no sapstain developed above 8%.

The composition according to the invention also has an effect comparable to that of sodium pentachlorophenate against mold fungi. Mold growth was markedly reduced at concentrations above 4%.

Moreover, the composition according to the invention had a surprisingly good effect against the thermotolerant mold Rhisopus sp. This fungus has proved to be quite resistant to a number of chemicals.

EXAMPLE 10

A field test was performed in Finland with the composition of Example 2 at various concentrations using sodium pentachlorophenate for comparison. Boards of freshly felled sawn timber were treated with the compositions and inspected about eight weeks later. At the inspection, each board was evaluated according to the following scale from 0 to 4:

Grade

0 = clean
1 = few small spots
2 = slightly stained or decayed
3 = moderately stained or decayed
4 = severely stained or decayed (more than half of the area of the board stained)

The results of the inspection are given in Table V. The table indicates the number of boards with various grades of damage. The percentage of the damaged boards with blue-stain molds and decay, respectively, are also recorded. The average index of damage is calculated as mean value of the grades of individual boards in a test group. For comparison, a commercial sodium pentachlorophenate (Na-PCP) preservative was used. Control boards were untreated.

TABLE V

| Composition | | Boards (Total) | Clean Pieces | Damaged Pieces in Grades 1 | 2 | 3 | 4 |
|---|---|---|---|---|---|---|---|
| Composition of Example 2 | 4% | 100 | 95 | 4 | 1 | 0 | 0 |
| | 8% | 99 | 94 | 5 | 0 | 0 | 0 |
| | 12% | 100 | 98 | 2 | 0 | 0 | 0 |
| Na—PCP | 1% | 100 | 97 | 3 | 0 | 0 | 0 |
| | 2% | 100 | 0 | 0 | 0 | 0 | 0 |
| Control (untreated) | | 96 | 22 | 19 | 22 | 6 | 27 |

| Composition | | Type of damage % blue-stain | mold | decay | Average Index of damage |
|---|---|---|---|---|---|
| Composition of Example 2 | 4% | 20 | 80 | 0 | 0.06 |
| | 8% | 20 | 100 | 0 | 0.05 |
| | 12% | 50 | 50 | 0 | 0.02 |
| Na—PCP | 1% | 100 | 0 | 0 | 0.03 |
| | 2% | 0 | 0 | 0 | 0 |
| Control (untreated) | | 99 | 55 | 47 | 1.97 |

EXAMPLE 11

A further field test was carried out in England as described in Example 10 using compositions of sodium dimethyldithiocarbamate (SDD) and borax in different proportions and comparing the results with various concentrations of sodium pentachlorophenate (NaPCP). The following scale of assessment was used:

Scale of Assessment

0 = none
1 = insignificant

2 = evident
3 = considerable
4 = severe
5 = ver severe

The results are set out in the following Table VI.

TABLE VI

| SDD 0.5% + 2% Borax | | | | | | | | | | |
|---|---|---|---|---|---|---|---|---|---|---|
| Stickered: Close | 0 0 0 0 1 | 0 0 0 1 1 | 2 2 1 0 0 | 0 0 0 3 1 | 0 0 0 0 3 | 0 2 2 1 0 | 1 1 1 1 0 | 1 1 0 0 0 | 2 2 2 1 0 | 1 1 0 0 0 |
| Stacked: | 3 3 3 3 0 | 2 1 1 1 1 | 3 3 3 2 1 | 4 4 4 3 3 | 1 4 2 4 3 | 2 4 3 3 1 | 0 0 3 1 3 | 1 1 1 3 1 | 4 2 0 3 1 | 3 4 2 0 1 |
| SDD 1% + 2% Borax | | | | | | | | | | |
| Stickered: Close | 0 0 0 0 0 | 2 2 2 0 0 | 0 0 0 0 0 | 2 2 0 0 0 | 0 0 0 0 0 | 3 1 0 0 0 | 2 0 0 0 0 | 2 2 0 0 0 | 2 2 0 0 0 | 1 1 1 0 0 |
| Stacked: | 1 1 1 0 0 | 1 1 0 0 0 | 1 0 0 0 0 | 2 1 1 0 0 | 1 0 0 0 0 | 1 0 0 0 0 | 1 1 0 0 0 | 1 3 2 3 1 | 3 3 3 2 1 | 3 3 2 2 1 |
| SDD 2% + 2% Borax | | | | | | | | | | |
| Stickered: Close | 0 0 0 0 0 | 0 0 0 0 0 | 0 0 0 0 0 | 0 0 0 0 0 | 1 0 0 0 0 | 0 0 0 0 0 | 1 1 0 0 0 | 1 0 0 0 0 | 0 0 0 0 1 | 0 0 0 0 0 |
| Stacked: | 2 1 0 0 0 | 2 0 0 0 0 | 1 0 0 0 0 | 1 1 0 0 0 | 2 2 1 0 0 | 2 2 0 0 0 | 2 2 0 0 0 | 1 0 0 0 0 | 1 1 0 0 0 | 0 0 0 0 0 |
| N.B. No basidiomycetes in any treatments. | | | | | | | | | | |
| CONTROLS | | | | | | | | | | |
| Stickered: Close | 5 5 5 5 5 | 5 5 5 5 5 | 5 5 5 5 5 | 4 5 5 5 5 | 4 4 5 5 5 | 5 5 5 5 5 | 5 5 5 5 5 | 5 5 5 5 5 | 5 5 5 5 5 | 5 5 5 5 5 |
| Stacked: | 5 5 5 5 5 | 5 5 5 5 5 | 5 5 5 5 5 | 5 5 5 5 5 | 5 5 5 5 5 | 5 5 5 5 5 | 5 5 5 5 5 | 5 5 5 5 5 | 5 5 5 5 5 | 5 5 5 5 5 |
| N.B. + considerable basidiomycetes in all controls. | | | | | | | | | | |
| NaPCP 0.5% | | | | | | | | | | |
| Stickered: Close | 1 1 0 0 0 | 1 1 0 0 0 | 1 1 1 0 0 | 1 1 1 1 1 | 1 1 1 2 1 | 1 1 0 0 0 | 1 1 2 1 1 | 1 2 2 0 0 | 2 2 2 2 2 | 3 2 2 1 0 |
| Stacked: | 2 2 3 3 3 | 3 3 2 2 1 | 2 2 3 3 1 | 2 2 2 3 3 | 2 3 4 3 2 | 1 4 3 3 2 | 3 3 1 3 3 | 2 3 2 3 3 | 2 1 3 3 1 | 2 2 1 1 1 |
| NaPCP 1% | | | | | | | | | | |
| Stickered: Close | 0 0 0 0 0 | 0 0 0 0 0 | 0 0 0 0 0 | 0 0 0 0 0 | 1 1 0 0 0 | 2 0 0 0 0 | 1 1 1 0 0 | 2 0 0 0 0 | 0 0 0 0 0 | 2 1 1 0 0 |
| Stacked: | 1 1 1 0 0 | 1 1 0 0 0 | 1 1 1 0 0 | 1 1 0 0 0 | 1 1 2 0 0 | 2 1 0 0 0 | 2 2 1 0 0 | 2 2 1 0 0 | 2 3 2 0 0 | 1 1 2 0 0 |
| NaPCP 2% | | | | | | | | | | |
| Stickered: Close | 0 0 0 0 0 | 0 0 0 0 0 | 0 0 0 0 0 | 0 0 0 0 0 | 1 1 0 0 0 | 1 1 1 0 0 | 0 0 0 0 0 | 0 0 0 0 0 | 0 0 0 0 0 | 0 0 0 0 0 |
| Stacked: | 0 0 0 0 0 | 1 0 0 0 0 | 0 0 0 0 0 | 1 1 0 0 0 | 2 0 0 0 0 | 3 0 0 0 0 | 0 0 0 0 0 | 2 1 0 0 0 | 0 0 0 0 0 | 0 0 0 0 0 |

Examples 9, 10 and 11 show that the compositions according to the present invention compare favorably with the known preservative, sodium pentachlorophenate, and has the important advantage over this known preservative in that the compositions according to this invention are much less hazardous to both man and environment.

EXAMPLE 12

Aqueous solutions were made up to 100 ml. volume which consisted of 2% w/v sodium dimethyldithiocarbamate, 2.798 g. $NaBO_2.4H_2O$ and
 (a) 0.5% w/v sodium isopropyl xanthate
 (b) 0.3% w/v sodium sulfite
 (c) 0.5% w/v sodium sulfite or
 (d) 0.1% w/v sodium sulfite All systems had a pH of 10.1–10.8. Each solution was placed in a u.v. cabinet and left for 9 days during which the solutions were at a temperature of about 30° C. A control containing no stabilizer was also included in the test. The following results were obtained:

| Solution | Appearance |
|---|---|
| a | 3 |
| b | 6 |
| c | 1 |
| d | 10 |
| Control | 10 |

Scale:
1–10
where
1 = no precipitation and
10 = heavy precipitation.

Example 12 shows the favorable effect of the stabilizers in preventing precipitation due to photochemical and/or thermal effects.

Various changes and modifications of the invention can be made, and to the extent that such variations incorporate the spirit of this invention, they are intended to be included within the scope of the appended claims.

What is claimed is:

1. A wood preservative composition for controlling sapstain and superficial mold comprising as active ingredient a mixture of an alkali metal borate and a dithiocarbamate of the formula:

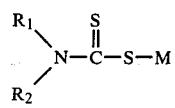

wherein $R_1$ and $R_2$ are each selected from hydrogen and alkyl containing 1 to 5 carbon atoms and M represents an alkali metal, an ammonium group or a lower alkyl substituted ammonium group, in which said alkali metal borate and dithiocarbamate are present in a ratio of 3:1 to 1:3 parts by weight, the alkali metal borate being expressed as anhydrous borax, and about 1 to 5 percent, based on said dithiocarbamate, of a stabilizer selected from sodium sulfite, potassium metabisulfite, and sodium lower alkyl xanthates.

2. A wood-preservative composition according to claim 1, comprising 0.5 to 2.5 parts by weight of the dithiocarbamate to 1 part by weight of alkali metal borate, expressed as anhydrous borax.

3. A wood-preservative composition according to claim 1, in which said stabilizer is selected from sodium sulfite and potassium metabisulfite.

4. A wood-preservative composition according to claim 1, which includes a gelling agent.

5. A wood-preservative composition according to claim 1, comprising sodium dimethyldithiocarbamate, sodium metaborate, anhydrous sodium sulphite and, as gelling agent, a derivative of carboxymethyl cellulose.

6. A wood-preservative composition according to claim 5, in which the weight ratio of said dithiocarbamate to borate is 0.5–2.5 to 1.

7. A method of preventing or inhibiting the infection of wood raw material by fungi which cause sapstain, superficial mold and decay which comprises contacting the wood raw material with a wood-preservative composition comprising as active ingredient a mixture of alkali metal borate and dithiocarbamate of the formula:

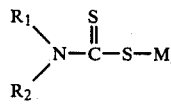

wherein $R_1$ and $R_2$ are each selected from hydrogen and alkyl containing 1 to 5 carbon atoms and M represents an alkali metal, an ammonium group or a lower alkyl substituted ammonium group, in which said alkali metal borate and dithiocarbamate are present in a ratio of 3:1 to 1:3 parts by weight, the alkali metal borate being expressed as anhydrous borax, and about 1 to 5 percent, based on said dithiocarbamate, of a stabilizer selected from sodium sulfite, potassium metabisulfite, and sodium lower alkyl xanthates.

8. A method of preventing or inhibiting the infection of wood raw material according to claim 7, wherein the composition is in the form of a solution or gel and has a pH above 10.

9. A method of preventing or inhibiting the infection of wood raw material according to claim 7 wherein the composition is in the form of a solution or gel containing from 0.5 to 5.0% w/v of the dithiocarbamate, from 0.25 to 2.5% w/v of the alkali metal borate expressed as anhydrous borax, in which the weight ratio of borate to dithiocarbamate is in the range of 3:1 to 1:3, and from 0.3 to 0.6% w/v of sodium sulfite.

10. A method according to claim 7 in which said stabilizer is selected from sodium sulfite and potassium metabisulfite.

11. The method according to claim 7 in which said ratio is about 1:1 parts by weight.

12. A method according to claim 7 in which said stabilizer is potassium metabisulfite.

13. A method according to claim 7 in which said stabilizer is sodium sulfite.

14. A composition according to claim 1 in which said alkali metal borate is borax.

15. A composition according to claim 1 in which said alkali metal borate is a potassium metaborate.

16. A composition according to claim 1 in which said dithiocarbamate is sodium dimethyldithiocarbamate.

17. A composition according to claim 1 in which said ratio is about 1:1 parts by weight.

18. The composition according to claim 1 in which said stabilizer is sodium isopropyl xanthate.

19. A composition according to claim 1 in which said stabilizer is potassium metabisulfite.

20. A composition according to claim 1 containing the following parts by weight:

| | |
|---|---|
| potassium metaborate | 15.5 |
| sodium dimethyldithiocarbamate | 20.0 |
| potassium metabisulfite | 0.9 |
| water | 63.6 |

21. The composition according to claim 20 having a pH of above 10.

* * * * *